US009523673B2

(12) United States Patent
Thiruvengadam

(10) Patent No.: US 9,523,673 B2
(45) Date of Patent: Dec. 20, 2016

(54) METHODS FOR DIAGNOSING AND IDENTIFYING MODULATORS OF MEMBRANE POTENTIALS IN BIPOLAR DISORDER AND ATTENTION DEFICIT HYPERACTIVITY DISORDER

(75) Inventor: Alagu P. Thiruvengadam, Ellicott City, MD (US)

(73) Assignee: PsychNostics, LLC, Ellicott City, MD (US)

(*) Notice: Subject to any disclaimer, the term of this patent is extended or adjusted under 35 U.S.C. 154(b) by 126 days.

(21) Appl. No.: 14/236,787

(22) PCT Filed: Sep. 14, 2012

(86) PCT No.: PCT/US2012/055356
§ 371 (c)(1),
(2), (4) Date: Apr. 29, 2014

(87) PCT Pub. No.: WO2013/052258
PCT Pub. Date: Apr. 11, 2013

(65) Prior Publication Data
US 2014/0248652 A1    Sep. 4, 2014

Related U.S. Application Data

(60) Provisional application No. 61/543,061, filed on Oct. 4, 2011, provisional application No. 61/653,579, filed on May 31, 2012.

(51) Int. Cl.
*G01N 33/50* (2006.01)
*G01N 33/68* (2006.01)

(52) U.S. Cl.
CPC ........ *G01N 33/502* (2013.01); *G01N 33/5008* (2013.01); *G01N 33/6872* (2013.01); *G01N 2333/912* (2013.01); *G01N 2800/304* (2013.01); *G01N 2800/305* (2013.01)

(58) Field of Classification Search
CPC .............. G01N 33/502; G01N 33/5008; G01N 33/6872; G01N 2800/305; G01N 2800/304; G01N 2333/912
See application file for complete search history.

(56) References Cited

U.S. PATENT DOCUMENTS

| 6,653,100 B1 | 11/2003 | Chandy et al. |
| 7,906,300 B2 | 3/2011 | Thiruvengadam et al. |
| 2008/0003181 A1 | 1/2008 | Sun et al. |
| 2010/0113358 A1 | 5/2010 | Tezapsidis et al. |
| 2011/0010780 A1 | 1/2011 | Pohlner et al. |

FOREIGN PATENT DOCUMENTS

WO    2007/093624 A2    8/2007

OTHER PUBLICATIONS

Joiner et al. hSK4, a member of a novel subfamily of calcium-activated potassium channels. Proc. Natl. Acad. Sci. USA vol. 94, pp. 11013-11018, Sep. 1997.*
International Search Report for PCT/US2012/055356, dated Dec. 17, 2012.

* cited by examiner

*Primary Examiner* — Taeyoon Kim
(74) *Attorney, Agent, or Firm* — Sughrue Mion, PLLC

(57) ABSTRACT

The present invention provides methods to modulate key elements along the DAG signaling pathway as well as a diagnostic assay, device and methods of using the same to diagnose bipolar disorder (BD) and attention deficit hyperactivity disorder (ADHD). Methods to identify diagnostic markers and drug targets for BD and ADHD. Methods of identifying effective compounds responsible for membrane potentials and excitabilities influencing bipolar disorder (BD) and attention deficit hyperactivity disorder (ADHD). Methods of identifying an effective compound that modulates the activity of Ca2+/CaM enzyme and compounds involved in changing the K+ gradient across the plasma membrane thereby increasing or decreasing the membrane potential ratio (MPR™) values. The invention provides methods of identifying a compound that modulates the activity of PKC which is an important protein of the DAG signaling pathway. Methods of identifying a compound that modulates DAG and its related enzymes along the DAG signaling pathway are provided. These compounds decrease or increase the membrane potential ratio (MPR™) in BD and ADHD patients.

15 Claims, 7 Drawing Sheets

**B 11-171
Effect of 8-CPT on MPR**

METHODS FOR DIAGNOSING AND IDENTIFYING MODULATORS OF MEMBRANE POTENTIALS IN BIPOLAR DISORDER AND ATTENTION DEFICIT HYPERACTIVITY DISORDER

FIELD OF THE INVENTION

The present invention relates to methods of diagnosing and identifying modulators of cellular membrane potential in patients with bipolar disorder (BD) and attention deficit hyperactivity disorder (ADHD), as well as methods of identifying modulators of cellular membrane potential in patients with BD and ADHD, to serve as diagnostic markers and drug targets for treatment of BD and ADHD. The present invention relates to methods of identifying modulators of the diacylglycerol (DAG) signaling pathway as diagnostic markers for diagnosing BD and ADHD, and as drug targets for treatment of BD and ADHD.

BACKGROUND OF THE INVENTION

The present invention relates to the fields of electrophysiology, molecular biology and molecular medicine, and more specifically to regulation of neuronal membrane potentials and excitabilities involved in BD and ADHD by polypeptides in the diacylglycerol signaling pathway, and modulation of the same.

The present invention relates to a method of identifying the modulators of the membrane potentials of patients' cells that could serve as the drug targets for decreasing the membrane potential ratio (MPR™) values in ADHD patients and for lowering the MPR™ values to the levels of the MPR™ values of negatives. The invention relates to a method of identifying the modulators of the membrane potentials of patients' cells that could serve as the drug targets for increasing the MPR™ values in BD patients and for raising the MPR™ values to the levels of the MPR™ values of negatives. This invention further identifies the DAG signaling pathway as a principal signaling mechanism that modulates the MPR™ values. Furthermore this invention identifies modulators such as compounds and polypeptides along this pathway as diagnostic markers and drug targets for BD and ADHD. They include DAG and its associated enzymes and kinases, PKC isoforms and associated enzymes and kinases, and $Ca^{2+}$/CaM and its associated enzymes and kinases.

It is well recognized that mental disorders are caused by the malfunction of the neurons in the brain. Neurons communicate with each other through electrophysiological signals. These signals are generated and modulated by the membrane potential and the excitability of the neurons. The identification of the molecules that modulate the signaling pathways in the neuronal cell is essential in diagnosing and treating mental illness. The membrane potential is the electrical potential difference (voltage) across a cell's membrane. Membrane potential results from the action of $K^+$ ion channels present in the membrane which along with the Na, K-ATPase enzyme maintain viable ion concentrations inside the cell.

Unlike most cells, neurons are electrically active and use changes in membrane potential for fast communication with other neurons. Neurons process and transmit information in the form of electrical signals. $K^+$ ion channels in the neuronal membrane set the membrane potentials and the excitability. These signals are then processed, amplified and transmitted to the synapse releasing the neurotransmitters. These transmitters again send a signal through their specific G-protein coupled receptors (GPCR) in the membrane of the target neuron. The GPCRs transmit these signals through two primary signal transduction pathways that process and transmit this signal to the $K^+$ ion channels in its membrane. These two pathways are the cAMP signaling pathway and the DAG signaling pathway (Nahorski S. R. British Journal of Pharmacology (2006) 147, S38-S45).

Calculations of the membrane potentials (MP) using Goldman-Hodgkin-Katz equation showed that lithium would depolarize the membrane potentials (Thiruvengadam, A. Journal of Affective Disorders 65 (2001) 95-99). This result led to the hypothesis that lithium's therapeutic efficacy was due to this depolarizing effect. This result was supported by earlier experimental and clinical results (Yonemura, K, and Sato, M, The Japanese Journal of Physiology, 1967; 17: 678-97), Grafe, et al, Brain Research, 1983; 279: 65-76 and El-Mallakh, et al, J. Affective Disorders, 1996; 41: 33-3). Thiruvengadam (Focus on Bipolar Disorder Research ISBN 1-59454-059-4 Editor: Malcomb R. Brown, pp. 15-35© 2005 Nova Science Publishers, Inc.) further showed that lithium not only depolarizes the membrane potential but also reduces the excitabilities of neurons. Measurement of membrane potentials of cultured lymphoblasts collected from BD patients showed that the membrane potential was hyperpolarized confirming the measurements of El Mallakh et al. In order to use the membrane potential as a diagnostic marker for BD, a ratiometric method was developed and used successfully for diagnosing BD patients (U.S. Pat. No. 7,425,410 B2 which is incorporated herein in its entirety) using their red blood cells (RBC). This method involves the measurement of MP from changes that occur in the $Na^+K^+$ ATPase activity in cells, in two buffers and taking the ratio of these two MPs. These experiments involve a test buffer that contains no $K^+$ ions but contains ethyl alcohol (EtOH). The membrane potentials are measured in the test buffer and compared with the membrane potentials measured in a reference buffer without EtOH. This ratio is called the membrane potential ratio (MPR™). It was further discovered that the membrane potential ratio (MPR™) could also be used to diagnose ADHD patients (U.S. Pat. No. 7,906,300 B2 which is incorporated herein in its entirety). To date, more than 550 patients have been tested using membrane potential ratio (MPR™). A summary of these test results is shown in FIG. 1. The membrane potential ratio (MPR™) values for BD patients were significantly lower than that for negatives (including normals, unipolar depressives, and schizophrenics). On the other hand, the membrane potential ratio (MPR™) values for ADHD patients were significantly higher than that for negatives as shown in FIG. 1.

It is essential to understand the biological basis for these differences in order to determine the scientific mechanism(s) and pathway(s) responsible for the differences in the membrane potential ratio (MPR™) among the three groups and to elucidate the pathophysiology of these illnesses.

Currently drug development efforts utilize neurotransmitters, their release, uptake and activation of their receptors as therapeutic drug targets for BD and ADHD. However, these drug targets do not serve as diagnostic biomarkers. The mechanism of action of drugs like lithium, amphetamine and anticonvulsants such as valproate and carbamazepine are not well understood. The results that the membrane potential ratio (MPR™) values for BD patients are significantly lower than those for negatives (including normals, unipolar depressives, and schizophrenics) and that the membrane potential ratio (MPR™) values for ADHD patients are significantly higher than those for negatives (as shown in FIG. 1) are very significant since they for the first time directly connect the specific patients with mental disorders to the specific biomarkers via changes that occur in the $Na^+K^+$ ATPase regulation and membrane potential changes therein. An understanding of the signaling pathway and the identification of the polypeptides and compounds modulating $Na^+K^+$ ATPase regulation was essential in advancing and enabling the diagnosis of BD and ADHD. To date, there are no studies in the art that connect the signaling pathway, the polypeptides involved, electrophysiological parameters such as membrane potentials and excitabilities with mental disorders such as BD and ADHD. The present invention accomplishes this objective leading to better diagnostics and therapeutics.

CAK Channels and Membrane Potentials In RBC: Although the expression of one of the small conductance family of CAK channels in RBC has been known since 2003 (Hoffman et al, PNAS, 100(12): 7366-7371 (2003); which is incorporated herein in its entirety), there has been no measurement of the membrane potential in RBC much more an observation of the differences among three groups of patient populations (negatives, BD and ADHD). The observation that EtOH hyperpolarizes the membrane potentials has been recognized in the art as a new discovery. However, only experiments using channel blockers, quinine and clotrimazole in RBC established this fact. No other literature in the art shows a connection between calcium-activated potassium (CAK) channels and ethanol, nor the involvement of CAK channels and cellular membrane potentials.

$Ca^{2+}$/CaM Activation of CAK Channels, EtOH and Membrane Potentials in RBC: It is well-known in the art that CAK channels are activated by calcium-calmodulin ($Ca^{2+}$/CaM). However, there is nothing in the art demonstrating the modulation of membrane potentials by either ethanol or by a calmodulin (CaM) activator such as calmodulin (CaM) Kinase II.

PKC, CaM and membrane potentials: It is well-known in the art that PKC through the DAG signaling pathway activates calmodulin (CaM). However, no studies in the art have shown that DAG signaling pathway modulates the CaK channels and membrane potentials.

DAG, CAK Channels and MP: DAG and the DAG signaling pathway has not been shown or understood in the art to have an effect on membrane potentials, much more be involved in the diagnosis of BD and ADHD. For instance, U.S. Pat. No. 6,593,121 2003 to Caricasole et al. (which is incorporated herein by reference in its entirety) relates to human diacylglycerol kinase proteins (hDAGK), and does not address membrane potential ratio (MPR™) differences nor modulation of the membrane potential ratio by the DAG pathway. Baum et al., Mol. Psychiatry 13(2): 197-207 (2008) was a genome-wide association study that implicated the diacylglycerol kinase eta (DGKH) and several other genes in the etiology of BD. However, Baum did not recognize that membrane potential ratios (MPR™) may be modulated by the DAG signaling pathway.

Thus, the present investigator identified an unaddressed need in the art, to determine the signaling pathway(s) and drug targets of the signaling pathway(s) that regulate cellular membrane potentials to provide a more specific means of identifying compounds that bind to these drug targets and modulate the interaction of these drug targets. These signaling pathways and drug targets can then be used for diagnostic and therapeutic purposes. For instance, the drug targets may be polypeptides involved in the diacylglycerol signaling pathway.

The present invention satisfies this need and provides related advantages as well. For example, this invention traces the pathway for BD and ADHD from the G-protein coupled receptors (GPCR) to the $K^+$ channel in patients' cells. The present discovery provides a better understanding of the pathophysiology of these disorders and a better means to diagnosis and treat BD and ADHD.

SUMMARY OF THE INVENTION

The present invention exploits the modulation of membrane potentials in cells of patients of BD and ADHD by the diacylglycerol signaling pathway, as well as identification of modulators of the pathway as diagnostic biomarkers and as targets for drug development.

The membrane potential in cells from ADHD and BD patients are significantly different than the membrane potential in cells from unaffected controls and siblings. For example, the membrane potentials of bipolar lymphoblasts are significantly hyperpolarized when compared with those of siblings and negative controls, whereas the membrane potentials of ADHD lymphoblasts are significantly depolarized when compared to those of siblings and negative controls. The changes in membrane potential reflect changes in modulators that regulate the diacylglycerol pathway in cells of patients affected with BD and ADHD.

This invention provides the methods for identifying the effective compounds that modulate the DAG signaling pathway which controls the Calcium Activated Potassium (CAK) channels responsible for the membrane potentials and excitabilities influencing bipolar disorder (BD) and attention deficit hyper activity disorder (ADHD).

This invention also provides a method of identifying an effective compound that modulates the activity of $Ca^{2+}$/CaM enzyme changing the $K^+$ gradient across the plasma membrane thereby increasing or decreasing the membrane potential ratio (MPR™) values.

This invention provides a method of identifying a compound that modulates the activity of PKC which is an important protein along the DAG signaling pathway.

This invention further provides a method to identify a compound that modulates the DAG and its related enzymes along the DAG signaling pathway. These compounds in turn decrease or increase the membrane potential ratio (MPR™) in BD and ADHD patients.

This invention also provides a method to modulate the key elements along the DAG signaling pathway and thus provide better diagnostic markers and drug targets for BD and ADHD.

The invention provides a method of diagnosing bipolar disorder (BD) in a human patient. The method involves obtaining a test ratio of a mean membrane potential of human patient cells incubating a first population of the human patient cells in vitro in the presence of an agent that alters diacylglycerol signaling and in the absence of $K^+$, to a mean membrane potential of a second population of the human patient cells incubated in vitro in the absence of the agent and presence of $K^+$. The test ratio is compared to (a) and/or (b): in which (a) is a control ratio of a mean membrane potential of control human cells known to not have said BD, and (b) is a bipolar control ratio of a mean membrane potential of bipolar control human cells known to have BD.

The invention also provides a method of diagnosing attention deficit hyperactivity disorder (ADHD) in a human patient. The method involves obtaining a test ratio of a mean membrane potential in the presence of an agent that alters diacylglycerol signaling and in the absence of $K^+$, to a mean membrane potential of a second population of the human patient cells incubated in vitro in the absence of the agent and presence of $K^+$. The test ratio is compared to (a) and/or (b): in which (a) is a control ratio of a mean membrane potential of control human cells known to not have said ADHD, and (b) is a ADHD control ratio of a mean membrane potential of ADHD control human cells known to have ADHD.

In a preferred embodiment, the agent that alters diacylglycerol signaling is selected from the group consisting of a calcium-calmodulin ($Ca^{2+}$/CaM) kinase inhibitor and a diacylglycerol kinase inhibitor.

In another preferred embodiment, the agent affects calcium-activated potassium (CaK) channels).

The invention further provides a method of identifying an agent for treatment of bipolar disorder (BD). The method involves combining a first population of human patient cells and a test agent suspected of altering human calcium-activated potassium channels $hSK_4$ activity. Obtaining a test ratio of a mean membrane potential of the first population of human patient cells incubated in vitro in the presence of the test agent and the presence of $K^+$ or absence of $K^+$, to a mean membrane potential of a second population of the human patient cells incubated in vitro in the absence of the test agent and the presence of $K^+$ or absence of $K^+$. The test ratio is compared to (a) and/or (b): in which (a) is a control ratio of a mean membrane potential of control human cells known to not have said BD, and (b) is a bipolar control ratio of a mean membrane potential of bipolar control human cells known to have said BD. When the test ratio is not significantly different from the control ratio of (a), the test ratio is increased towards the control ratio in comparison to the bipolar control ratio of (b), or the test ratio is increased in comparison to the bipolar ratio of (b), the test agent is determined to modulate the mean membrane potential in BD patients.

In a preferred embodiment, the agent is selected from the group consisting of a calcium-calmodulin ($Ca^{2+}$/CaM) kinase inhibitor and a diacylglycerol kinase inhibitor.

In another embodiment, the agent is a calcium-calmodulin ($Ca^{2+}$/CaM) kinase inhibitor. Specifically, autocamtide-2-related inhibitory peptide (AIP).

In another embodiment, the agent is a diacylglycerol kinase inhibitor. Specifically, 6-[2-[4-[(4-fluorophenyl)phenylmethylene]-1-piperidinyl]ethyl]-7-methyl-5H-thiazolo[3,2-a]pyrimidin-5-one (ALX).

The invention further provides a method of identifying an agent for treatment of attention deficit hyperactivity disorder (ADHD). The method involves combining a first population of human patient cells and a test agent suspected of altering human calcium-activated potassium channels $hSK_4$ activity. Obtaining a test ratio of a mean membrane potential of the first population of human patient cells incubated in vitro in the presence of the test agent and in the absence of $K^+$, to a mean membrane potential of a second population of the human patient cells incubated in vitro in the absence of the test agent and the presence of $K^+$ or absence of $K^+$. The test ratio is compared to (a) and/or (b): in which (a) is a control ratio of a mean membrane potential of control human cells known to not have said ADHD, and (b) is an ADHD control ratio of a mean membrane potential of ADHD control human cells known to have said ADHD. When the test ratio is not significantly different from the control ratio of (a), the test ratio is decreased towards the control ratio of (a) in comparison to (b), or the test ratio is decreased in comparison to the ADHD control ratio of (b), the test agent is determined to modulate the mean membrane potential in ADHD patients.

In a preferred embodiment, the agent is selected from the group consisting of a calcium-calmodulin ($Ca^{2+}$/CaM) kinase inhibitor, a diacylglycerol kinase inhibitor, and a protein kinase C inhibitor.

In another preferred embodiment, the agent is a PKC inhibitor selected from the group consisting of phorbol 12-myristate 13-acetate (PMA), 3-(1H-indol-3-yl)-4-[2-(4-methylpiperazin-1-yl)quinazolin-4-yl]pyrrole-2,5-dione (Sotrastaurin or AEB07), 13-hydroxyoctadecadienoic acid (13-HODE), aprinocarsen, bisindolylmaleimide, bryostatin-1, butein, calphostin C, 7,8-dihydroxycoumarin, 4'-demethylamino-4'-hydroxystaurosporine, rottlerin, ruboxistaurin, staurosporine, and verbascoside.

In another preferred embodiment, the agent is a calcium-calmodulin ($Ca^{2+}$/CaM) kinase inhibitor. Specifically, autocamtide-2-related inhibitory peptide (AIP).

In another preferred embodiment, the agent is a diacylglycerol kinase inhibitor. Specifically, 6-[2-[4-[(4-fluorophenyl)phenylmethylene]-1-piperidinyl]ethyl]-7-methyl-5H-thiazolo[3,2-a]pyrimidin-5-one (ALX).

Further, the invention provides a method of identifying an agent that modulates diacylglycerol signaling for the treatment of bipolar disorder (BD). The method involves combining a first population of human patient cells and a test agent suspected of altering diacylglycerol signaling. Obtaining a test ratio of a mean membrane potential of the first population of human patient cells incubated in vitro in the presence of the test agent and in the absence of $K^+$, to a mean membrane potential of a second population of the human patient cells incubated in vitro in the absence of the test agent and in the presence of $K^+$ or absence of $K^+$. The test ratio is compared to (a) and/or (b): in which (a) is a control ratio of a mean membrane potential of control human cells known to not have said BD, and (b) is a bipolar control ratio of a mean membrane potential of bipolar control human cells known to have said BD. When the test ratio is not significantly different from the control ratio of (a), the test ratio is increased towards the control ratio in comparison to the bipolar control ratio of (b), or the test ratio is increased in comparison to the bipolar ratio of (b), the test agent is determined to modulate the mean membrane potential in BD patients.

In addition, the invention provides a method of identifying an agent that modulates diacylglycerol signaling for the treatment of attention deficit hyperactivity disorder (ADHD). The method involves combining a first population of human patient cells and a test agent suspected of altering diacylglycerol signaling. Obtaining a test ratio of a mean membrane potential of the first population of human patient cells incubated in vitro in the presence of the test agent and in the absence of K+, to a mean membrane potential of a second population of the human patient cells incubated in vitro in the absence of the test agent and the presence of $K^+$ or absence of $K^+$. The test ratio is compared to (a) and/or (b): in which (a) is a control ratio of a mean membrane potential of control human cells known to not have said ADHD, and (b) is an ADHD control ratio of a mean membrane potential of ADHD control human cells known to have said ADHD. When the test ratio is not significantly different from the control ratio of (a), the test ratio is decreased towards the control ratio of (a) in comparison to (b), or the test ratio is decreased in comparison to the ADHD control ratio of (b), the test agent is determined to modulate the mean membrane potential in ADHD patients.

In a preferred embodiment, the human cells is selected from the group consisting of red blood cells and lymphoblasts.

In a more preferred embodiment, the invention provides for a method of identifying an agent for treatment of bipolar disorder (BD) in which the first population of human patient cells is combined with a test agent suspected of altering $Ca^{2+}$/CaM activation of calcium-activated potassium channels, the control human cells and the bipolar control human cells are incubated in vitro in the presence of autocamtide-2-related inhibitory peptide (AIP), the human cells are selected from the group consisting of red blood cells and lymphoblasts, and the $Ca^{2+}$/CaM activation of calcium-activated potassium channels depolarizes the mean membrane potential of the human patient cells.

In another more preferred embodiment, the invention provides for a method of identifying an agent for treatment of bipolar disorder (BD) in which the first population of human patient cells is combined with a test agent suspected of altering diacylglycerol kinase activity, the control human cells and the bipolar control human cells are incubated in vitro in the presence of 6-[2-[4-[(4-fluorophenyl)phenylmethylene]-1-piperidinyl]ethyl]-7-methyl-5H-thiazolo[3,2-a]pyrimidin-5-one (ALX), and the human cells are selected from the group consisting of red blood cells and lymphoblasts.

In yet another more preferred embodiment, the invention provides for a method of identifying an agent that modulates diacylglycerol signaling for the treatment of attention deficit hyperactivity disorder (ADHD) in which the first population of human patient cells is combined with a test agent suspected of altering PKC activity, the control human cells and the bipolar control human cells are incubated in vitro in the presence of phorbol 12-myristate 13-acetate (PMA), and the human cells are selected from the group consisting of red blood cells and lymphoblasts.

The present invention also relates to a kit that includes the buffers described herein, and preparation thereof. The kit may be a diagnostic kit for diagnosing ADHD or BD, or an agent identifying kit used for identifying a modulator of diacylglycerol signaling for the treatment of ADHD or BD. For instance, the modulator may include a calcium-calmodulin ($Ca^{2+}$/CaM) kinase inhibitor, a diacylglycerol kinase inhibitor, and a protein kinase C inhibitor. Preferably, the kit used for identifying a modulator that alters calcium-activated potassium channel activity such as $hSK_4$ channel activity.

In a preferred embodiment, the invention relates to a method of diagnosing bipolar disorder (BD) in a human patient in which a test ratio is obtained from a mean membrane potential of a first population of human patient cells incubated in vitro in the presence of an agent that alters $K^+$ channel activity and in the absence of $K^+$, to a mean membrane potential of a second population of the human patient cells incubated in vitro in the absence of the agent that alters $K^+$ channel activity and in the absence of $K^+$. The test ratio is compared to (a) and/or (b) in which (a) is a control ratio of a mean membrane potential of control human cells known to not have said BD incubated in vitro in the presence of the agent that alters $K^+$ channel activity and in the absence of $K^+$, to a mean membrane potential of the control human cells known to have said BD incubated in vitro in the absence of the agent that alters $K^+$ channel activity and in the absence of $K^+$, and (b) is a bipolar control ratio of a mean membrane potential of bipolar control human cells known to have said BD incubated in vitro in the presence of the agent that alters $K^+$ channel activity and in the absence of $K^+$, to a mean membrane potential of the bipolar control human cells incubated in vitro in the absence of the agent that alters $K^+$ channel activity and in the absence of $K^+$. The mean membrane potential is determined by incubating the cells in vitro in buffer comprising a potential-sensitive dye, resuspending the cells in potential-sensitive dye free-buffer, and measuring the cell fluorescence. The human patient is diagnosed to have bipolar disorder when the test ratio obtained is significantly lower than the control ratio obtained in (a) and/or the test ratio obtained is not significantly different from the bipolar control ratio obtained in (b).

In a preferred embodiment, the invention relates to a method of diagnosing attention deficit hyperactivity disorder (ADHD) in a human patient in which a test ratio is obtained of a mean membrane potential of a first population of human patient cells incubated in vitro in the presence of an agent that alters $K^+$ channel activity and in the absence of $K^+$, to a mean membrane potential of a second population of the human patient cells incubated in vitro in the absence of the agent that alters $K^+$ channel activity and in the absence of $K^+$. The test ratio is compared to (a) and/or (b) in which (a) is a control ratio of a mean membrane potential of control human cells known to not have said ADHD incubated in vitro in the presence of the agent that alters $K^+$ channel activity and in the absence of $K^+$, to a mean membrane potential of the control human cells known incubated in vitro in the absence of the agent that alters $K^+$ channel activity and in the absence of $K^+$, and (b) is a bipolar control ratio of a mean membrane potential of ADHD control human cells known to have said ADHD incubated in vitro in the presence of the agent that alters $K^+$ channel activity and in the absence of $K^+$, to a mean membrane potential of the ADHD control human cells incubated in vitro in the absence of the agent that alters $K^+$ channel activity and in the absence of $K^+$. The mean membrane potential is determined by incubating the cells in vitro in buffer comprising a potential-sensitive dye, resuspending the cells in potential-sensitive dye free-buffer, and measuring the cell fluorescence. The human patient is diagnosed to have ADHD when the test ratio obtained is significantly higher than the control ratio obtained in (a) and/or the test ratio obtained is not significantly different from the ADHD control ratio obtained in (b).

In an embodiment of the invention, the agent that alters $K^+$ channel activity includes, but is not limited to, ethanol, amphetamine, ephedrine, cocaine, caffeine, nicotine, methylphenidate, lithium, δ-9-tetrahydrocannibinol, phencyclidine, lysergic acid diethylamide (LSD), mescaline, or combinations thereof.

In a preferred embodiment, the agent that alters $K^+$ channel activity is ethanol.

DETAILED DESCRIPTION OF THE INVENTION

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "a human cell" means one human cell or more than one human cell.

The terms "agent(s)", "modulator(s)", "test agent(s)", and "compound(s)" are used herein interchangeably and are meant to include, but are not limited to, peptides, nucleic acids, carbohydrates, small organic molecules, and any other molecules (including, but not limited to, chemicals, metals, and organometallic compounds).

The present invention relates to methods for modulating the diacylglycerol signaling pathway. The present invention provides methods of identifying compounds for the treatment of BP and ADHD, as well as methods of treating BP and ADHD with the compounds identified. In this respect, the present invention provides methods for identifying targets for drug modulation of the diacylglycerol signaling pathway, and methods of identifying compounds that modulate these targets of the diacylglycerol pathway.

In the experiments described herein, the membrane potentials of human cells such as whole blood cells are ascertained and compared. However, the methods of the present invention may use any cell type, such as, but not limited to, erythrocytes, lymphoblasts, platelets, leukocytes, macrophages, monocytes, dendritic cells, fibroblasts, epidermal cells, mucosal tissue cells, cells in the cerebrospinal fluid, and hair cells. fs Preferably, cells in blood, skin cells, hair cells, or mucosal tissue cells are used because of the ease of harvesting these cell types.

Figure 1:
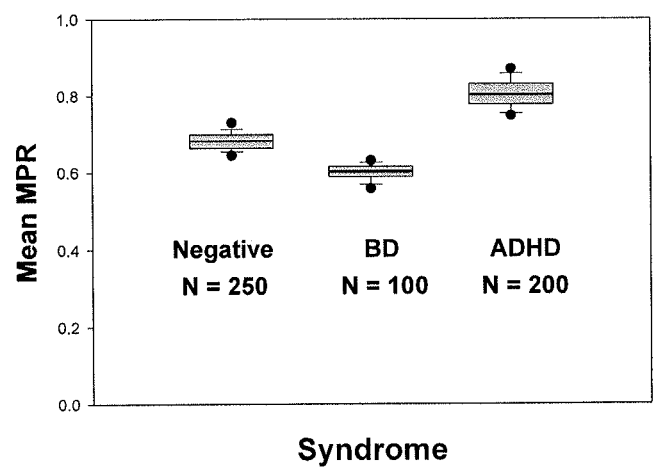
FIG. 1. Shows the mean values of membrane potential ratios (MPR™) for the three groups of patients including BD, ADHD and negatives (negatives do not have either BD or ADHD). The membrane potential ratios (MPR™) values are significantly different from each other. Until this study, the differences in the membrane potential ratio (MPR™) were unclear. The objectives of this invention are to determine the cause of this difference and to identify the modulator proteins leading to drug targets and diagnostic markers.

Membrane Potential Ratio (MPR™) Differences in BD and ADHD: As shown in FIG. 1 the mean values of membrane potential ratio (MPR™) for the BD patients are significantly lower than that for the Negatives (who are neither BD nor ADHD). Similarly the membrane potential ratio (MPR™) values for the ADHD patients are significantly higher than that for the negatives. It is essential to understand these differences so that the underlying pathophysiology of these disorders is better understood leading to better diagnostic markers and drug targets. "Significantly higher", "significantly lower" or "significantly different" means a value that is considered significant as determined by the various statistical tests and analyses commonly used and known in the art. Membrane potential ratio (MPR™) is the ratio between the membrane potential in the test buffer and that in the reference buffer. The reference buffer contains NaCl, $CaCl_2$, glucose and Hepes whereas the test buffer contains ethyl alcohol (EtOH) in addition to these compounds. Both buffers do not contain $K^+$ ions. The role of the absence of $K^+$ ions in the buffer on membrane potential and the addition of EtOH needs to be understood in order to explain their effects.

$K^+$ Free Buffer and $SK_4$ Channels: Gardos discovered as early as 1958 that the potassium permeability in RBCs is controlled by the calcium-activated potassium channel (CAK) called Gardos channel (Gardos, G., Biochim. Biophys. Acta. 30:653-54 (1958)). The Gardos channel has been confirmed as the KCNN4 (International designation for the calcium activated potassium channels; it is also called $hSK_4$ in humans) belonging to the family of slow conductance potassium channels (Joiner et al, Neurobiology, PNAS, 94: 11013-11018 (1997), which is incorporated herein in its entirety, and also Hoffman et al, PNAS, 100(12): 7366-7371) (2003)). Grygorczyk et al (BIOPHYS. J. Biophysical Society, 45: 693-698 (1984)) found that the net efflux of K+ is decreased significantly when RBCs are suspended in $K^+$ free buffer implying that the $hSK_4$ channels are closed in the absence of the extracellular $K^+$ ion.

Figure 2:
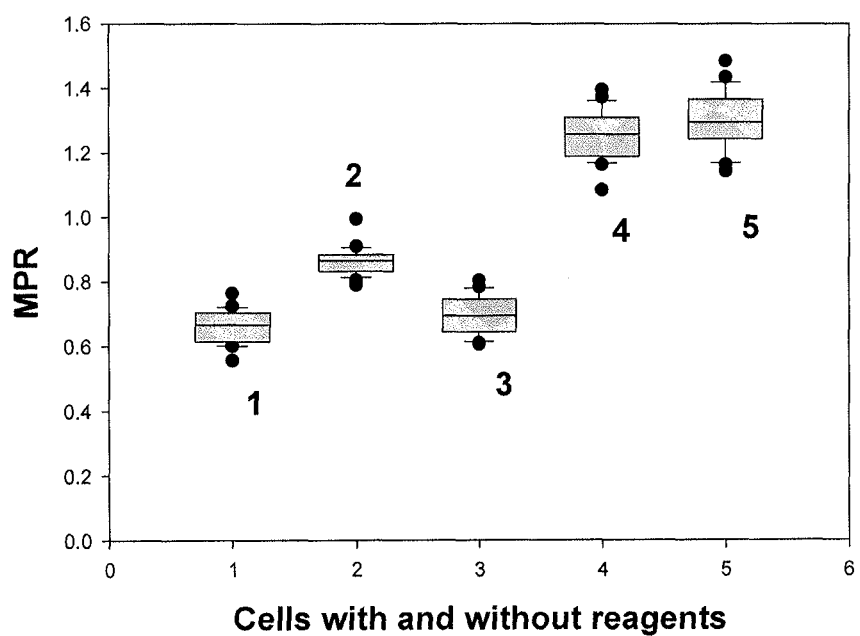
FIG. 2. Shows the effect of quinine and clotrimazole on membrane potential ratio (MPR™).

Effect of EtOH on $hSK_4$ Channel: Krjnevic speculated that ethanol, sedatives and hypnotic drugs activated the CaK channels (Krjnevic K (1972) Excitable membranes and anesthetics, in Cellular Biology and Toxicity of Anesthetics (Fink B R: ed, pp 3-9. Williams & Wilkins, Baltimore, Md.). Later on, it was shown that ethanol increased $K^+$ efflux in CAK channels. Mustonen et al., Scand. J. Gastroenterol. 39(2): 104-110 (2004)) showed that the ethanol effect was reversed by quinine, a CaK channel blocker (Reichstein E, Rothstein A., J Membr Biol. 59:57-63 (1981)). It is known that clotrimazole (CLTX) is also an effective blocker of CAK channels (Ohnishi S T, et al, Biochim Biophys Acta. 1010:199-203 (1989)). The experiments with $hSK_4$ blockers quinine and clotrimazole show that the EtOH effect is blocked by these $hSK_4$ channel blockers as shown in FIG. 2. Quinine and clotrimazole were added to the test buffer and the membrane potential ratio (MPR™) was determined. The membrane potential ratio (MPR™) values are shown in box plots (FIG. 2). Box 2 shows the increased values of membrane potential ratio (MPR™) with 1 mM quinine in the test buffer as compared to the values in box 3 for the test buffer without quinine. Similarly boxes 3, 4 and 5 show the results for CLTX.

Box 3 represents no CLTX, while box 4 for 2.5 micro molar CLTX and box 5 for 5 micro molar concentrations in the test buffer. These blockers depolarized the membrane potentials robustly indicating that the $hSK_4$ channels are responsible for the membrane potential ratio (MPR™) in these tests. This result teaches the POSA that the calcium activated potassium channels $SK_4$ (KCNN4) expressed in RBC are responsible for the membrane potentials observed in RBC. These experiments confirm that the EtOH opens the $hSK_4$ and lets the $K^+$ permeate out of the cell thereby hyperpolarizing the cell membrane.

This fact is further explained by the modified Goldman-Hodgkin-Katz equation (shown below) as derived by Thiruvengadam (Thiruvengadam, A. Journal of Affective Disorders 65 (2001) 95-99).

$$V = 62\log_{10} \frac{P_K/P_{Na}(K_o^+/Na_o^+) + 1}{P_K/P_{Na}(K_i^+/Na_o^+)}$$

This equation shows that the membrane potential V is a function of relative potassium permeability $P_K/P_{Na}$, extracellular potassium concentration $K_o$, intracellular potassium concentration $K_i$, and extracellular sodium concentration Na$_o$. Since the extracellular K$_o$ is zero, and Na$_o$ is constant, the membrane potential is solely a function of the intracellular K$_i$. If the intra cellular K$^+$ decreases due to the opening of the channel the cell membrane potential will hyperpolarize according to this equation, explaining the experimental observation.

hSK$_4$ Pore Structure and EtOH action: The calcium activated K$^+$ channel structure consists of six domains. SK channel family is a prime example of modular evolutionary protein design. The pore forming unit consists of the voltage sensing domains that are found in all other voltage gated K$^+$ channels, a pair of transmembrane domains involved in the Ca$^{2+}$-activated regulation of the K$^+$ conductance, and a unique large intracellular domain that acts as a sensor for the intracellular Ca$^{2+}$ concentration. The amino acid chain forms a transmembrane pore of about 6-8 angstroms through which the K$^+$ ion (4 angstroms) flows. The amino acid configuration and location regulates this flow rate and excitability of this channel. It is known that any mutations affecting the amino acids forming this pore would affect the K$^+$ currents and excitability (Yang Y et al, J Biol. Chem. 2010 Jan. 1; 285(1): 131-141). This pore is closed when RBCs are suspended in K$^+$ free buffer as shown by Grygorczyk et al (BIOPHYS. J. Biophysical Society, Volume 45, 1984, 693-698).

In order to confirm that the CAK channel opening and closing is involved in the membrane potential of the RBC used for the membrane potential ratio (MPR™) tests, the CAK channel blockers, quinine and clotrimazole were added to the test buffer and the membrane potential ratio (MPR™) was determined (FIG. 2). These blockers depolarized the membrane potentials robustly indicating the CAK closing and opening involvement in the membrane potential ratio (MPR™). This result establishes that the calcium activated potassium channels SK$_4$ (KCNN4) expressed in RBC are responsible for the membrane potentials observed in RBC. Addition of EtOH opens this pore and lets K$^+$ ions flow out thereby reducing the intra cellular K$^+$ concentration as discussed above. This reduction in the intra cellular K$^+$ concentration hyperpolarizes the cell membrane. As shown in FIG. 1 the hyperpolarized membrane potentials are significantly different for the three groups of patients who participated in the clinical trials.

Calmodulin (CaM): Calcium activated potassium channels (CAK channels of which SK$_4$ is a member) are activated by CaM (Fager G. M. et al., J. Biol. Chem. 274(9): 5746-5754 (1999)). Calmodulin, CaM (also called Ca$^{2+}$/CaM) is a widespread and abundant transducer of calcium signaling in cells (Stevens F C, Can. J. Biochem. Cell Biol. 61 (8): 906-10 (1983)). It can bind to and regulate a number of different protein targets, thereby affecting many different cellular functions. Calcium gating in small conductance calcium activated potassium channels (CAK channels) is the primary mechanism controlling the potassium flow through the pores. CaM is responsible for this calcium gating (Fager G. M. et al 1999, The J. Biolo. Chem. Vol. 274, No. 9, pp. 5746-5754). CAK channels are activated by Ca$^{2+}$/CaM signaling which modulates the opening and closing of hSK$_4$ channels. Ca$^{2+}$/CaM in turn are modulated by the following two important signaling pathways.

Figure 3:
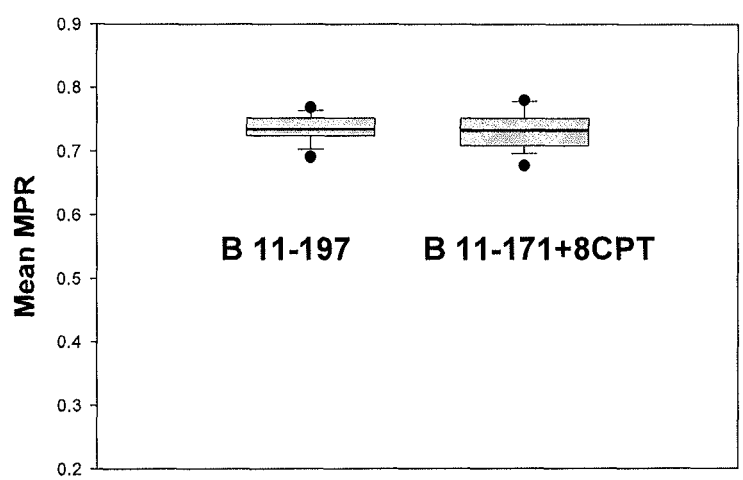
FIG. 3. Shows the effect of 8-CPT on membrane potential ratio (MPR™).

Signaling Pathways: These pathways are the cAMP pathway and the DAG pathway. These two important signaling pathways in the cell are activated by G-protein coupled receptors (GPCR), which receive the signal from external stimuli by ligands such as hormones, growth factors, cytokines, chemokines, neurotransmitters and neurotropins (Nahorski S. R. British Journal of Pharmacology (2006) 147, S38-S45).

cAMP Signaling Pathway: Cyclic adenosine monophosphate (cAMP, cyclic AMP or 3'-5'-cyclic adenosine monophosphate) is an important second messenger in many biological processes. The cAMP is derived from adenosine triphosphate (ATP) and is used for intracellular signal transduction in many different organisms. It works by activating the cAMP-dependent protein kinase called protein kinase A (PKA). The addition of cAMP analog 8-CPT promotes the PKA activity (Sandberg M. et al, Biochem. J. 279: 521-527 (1991)). In order to determine whether the cAMP pathway is involved in the membrane potential ratio (MPR™), 8-CPT-cAMP (50 µM) was added to the test buffer and the membrane potential ratio (MPR™) values were determined. There was no effect of 8-CPT on membrane potential ratio (MPR™) as shown in FIG. 3. This result showed that the cAMP pathway is not involved in the processes affecting the membrane potential ratio (MPR™).

DAG Signaling Pathway: In biological signaling, diacylglycerol (DAG) functions as a second messenger signaling lipid (Nahorski S. R. British Journal of Pharmacology (2006) 147, S38-S45). DAG is a product of the hydrolysis of the phospholipid PIP2 (phosphatidyl inositol-bisphosphate) by the enzyme phospholipase C (PLC) (a membrane-bound enzyme) that, through the same reaction, produces inositol trisphosphate (IP$_3$). Although inositol trisphosphate (IP$_3$) diffuses into the cytosol, diacylglycerol (DAG) remains within the plasma membrane, due to its hydrophobic properties. The production of DAG in the membrane facilitates translocation of PKC from the cytosol to the plasma membrane (Newton, A. C. Am J Physiol Endocrinol Metab 298:E395-E402, 2010). Hence both DAG and PKC enzymes play important roles in several signal transduction cascades.

Figure 4:
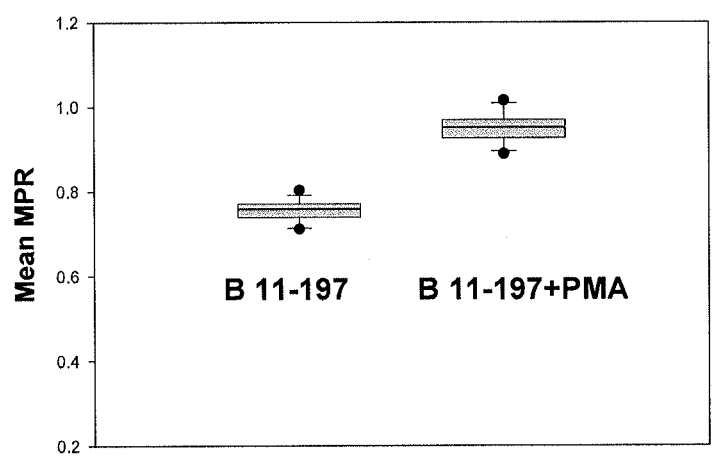
FIG. 4. Shows the effect of PMA on membrane potential ratio (MPR™).

PKC and Phorbol 12-Myristate 13-Acetate (PMA): PMA is a diester of phorbol often employed in biomedical research to activate the signal transduction enzyme protein kinase C (PKC) (Castagna et al 1982, Journal of Biological Chemistry 257 (13): 7847-7851). In order to see if the activation of PKC has any effect on membrane potential ratio (MPR™), PMA was added to the test buffer and the MPR™ was measured. As shown in FIG. 4, the MPR™ is indeed depolarized indicating the involvement of PKC in the hSK$_4$ activation. This figure shows a comparison of the MPR™ values with 2.5 µM PMA in the test buffer and those values without PMA. PMA depolarizes the cells very effectively.

Figure 5:
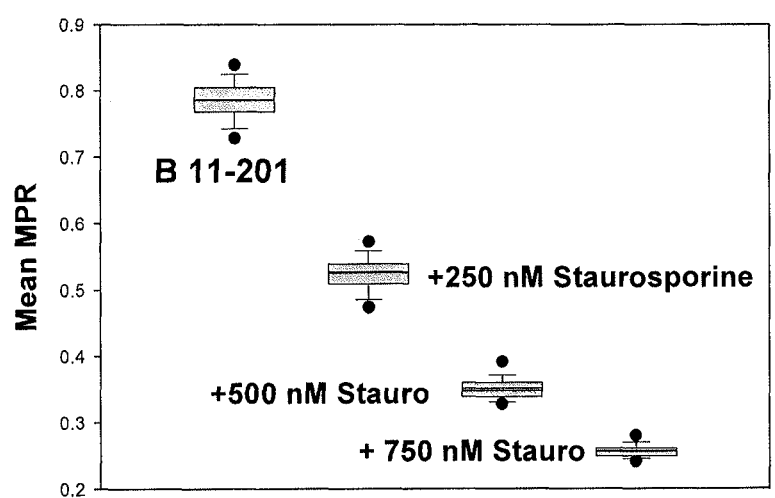
FIG. 5. Shows the effect of staurosporine on membrane potential ratio (MPR™).

Staurosporine: Staurosporine is a natural product originally isolated in 1977 from the bacterium *Streptomyces staurosporeus*. The main biological activity of staurosporine is the inhibition of protein kinases including PKC through the prevention of ATP binding to the kinase (Karaman M W, Nat. Biotechnol. 2008 January; 26(1):127-32). The PKC inhibitor staurosporine was added to the test buffer at three different concentrations and the membrane potential ratio (MPR™) values were determined and shown in FIG. 5. Staurosporine hyperpolarizes the membrane potentials very effectively indicating the role of PKC and the DAG pathway in membrane potentials. The effect of PKC inhibition on membrane potential ratio (MPR™) is shown in FIG. 5. As shown in this figure, staurosporine hyperpolarizes the membrane potential in a concentration dependent manner.

CaM Kinase II: As discussed earlier, calcium gating in small conductance calcium activated potassium channels (CaK channels) is the primary mechanism controlling the potassium flow through the pores. CaM is responsible for this calcium gating (Fager G. M. et al., J. Biol. Chem. 274(9): 5746-5754 (1999)). CaM Kinase II is regulated by the $Ca^{2+}$/calmodulin complex and is involved in many signaling cascades. CaM Kinase II is found in high concentrations in neuronal synapses, and in some regions of the brain it may constitute up to 2% of the total protein content. Activation of CaM kinase II has been linked to memory and learning processes in the vertebrate nervous system. The effects of $Ca^{2+}$ are also important. It cooperates with DAG in activating PKC and can activate the CaM kinase pathway, in which calcium modulated protein, calmodulin binds to $Ca^{2+}$, undergoes a change in conformation, and activates CaM kinase II, which has a unique ability to increase its binding affinity to CaM by making CaM unavailable for the activation of other enzymes. In order to see the involvement of $Ca^{2+}$/CaM/Cam Kinase II in membrane potential ratio (MPR™), the CaM Kinase inhibitor was investigated.

CaM Kinase II Inhibitor AIP: A novel synthetic peptide AIP (Autocamtide-2-related Inhibitory Peptide), a nonphosphorylatable analog of autocamtide-2, was found to be a highly specific and potent inhibitor of calmodulin-dependent protein kinase II (CaM-kinase II) (Ishida et al, J. Biol. Chem. 270, 2163 (1995)). AIP (myristoylated) is the same as AIP but is N-terminal myristoylated to increase cell permeability. AIP depolarizes the membrane robustly at a 5 micro M concentration as shown in FIG. 6 again establishing the DAG pathway as the primary signaling process.

DAG Kinase Inhibitor: Diacylglycerol kinase (DGK) is a family of enzymes that catalyzes the conversion of diacylglycerol (DAG) to phosphatidic acid (PA) utilizing ATP as a source of the phosphate. In non-stimulated cells, DGK activity is low allowing DAG to be used for glycerophospholipid biosynthesis but on receptor activation of the phosphoinositide/DAG pathway, DGK activity increases driving the conversion of DAG to PA. As both lipids are thought to function as bioactive lipid signaling molecules with distinct cellular targets, DGK therefore occupies an important position, effectively serving as a switch by terminating the signaling of one lipid while simultaneously activating signaling by another (Merida et al Biochem. J. (2008) 409, 1-18). DAG Kinase inhibitor, ALX, (6-[2-[4-[(4-fluorophenyl)phenylmethylene)-1-piperidinyl]ethyl]-7-methyl-5H-thiazolo[3,2-a]pyrimidin-5-one) was found to inhibit diacylglycerol kinase in human red blood cell membranes (de Courcelles et al., J. Biol. Chem. 260(29): 15762-15770 (1985)). ALX depolarizes the membrane potential as shown in this figure at three different concentrations including 2.5 µl, 5 µl and 7.5 µl.

Cause of the differences in membrane potential ratio (MPR™): FIG. 1 shows that there are differences in the mean values of MPR™ for the negatives, BDs, and ADHDs. Those skilled in the art recognize that these differences arise from the differential modulation of the DAG pathway in the patients with these disorders. For example a genome-wide association study implicated the diacylglycerol kinase eta (DGKH) and several other genes in the etiology of bipolar disorder (Baum et al, Mol. Psychiatry. 13(2): 197-207 (2008)). In the Baum study, the authors found that, out of 37 SNPs selected for individual genotyping, the strongest association signal was detected at a marker within the first intron of DGKH. Similarly PKC has been implicated in BD by several authors (Hahn and Friedman, Bipolar Disorders 1999:2:81-86).

However, these authors failed to recognize the important role of the DAG pathway for modulating membrane potentials and excitabilities in these disorders. Moreover, the cells from actual patients could be used to trace this pathway and show how these three groups of patients differ from each other. The present inventor has recognized that this pathway could be used to develop diagnostic markers and therapeutic drugs using the patient cells instead of animal models. Also, the use of the DAG pathway opens the way to modulate the several molecules that affect this pathway.

In one embodiment of the present invention, the agent that alters diacylglycerol signaling may be selected from, but not limited to, calcium-calmodulin ($Ca^{2+}$/CaM) kinase inhibitors, calcium-calmodulin ($Ca^{2+}$/CaM) promoters, diacylglycerol kinase inhibitors, protein kinase C inhibitors, calcium-calmodulin ($Ca^{2+}$/CaM) antagonists, and calcium-calmodulin ($Ca^{2+}$/CaM) promoters.

For instance, the PKC inhibitor may be selected from, but not limited to, phorbol 12-myristate 13-acetate (PMA), 3-(1H-indol-3-yl)-4-[2-(4-methylpiperazin-1-yl)quinazolin-4-yl]pyrrole-2,5-dione (Sotrastaurin or AEB07), β-hydroxyoctadecadienoic acid (13-HODE), aprinocarsen, bisindolylmaleimide, bryostatin-1, butein, calphostin C, 7,8-dihydroxycoumarin, 4'-demethylamino-4'-hydroxystaurosporine, rottlerin, ruboxistaurin, staurosporine, and verbascoside.

For instance, calcium-calmodulin ($Ca^{2+}$/CaM) antagonists may be selected from, but not limited to A-7 hydrochloride, calmidazolium chloride (R24571), E6 berbamine, fluphenazine-N-2-chloroethane.2HCl, J-8 hydrochloride, trifluoperazine.2HCl (Stelazine), phenothiazine, phenoxybenzamine, W-13 Isomer hydrochloride, decyl analog hydrochloride, W-5, and W-7.

For instance, calcium-calmodulin ($Ca^{2+}$/CaM) promoters may be selected from, but not limited to, CaM (G-3), CaM (N-19), CaM (L-20), CaM (FL-149), and CaM (H-149).

For instance, calcium-calmodulin ($Ca^{2+}$/CaM) kinase inhibitors may be selected from, but not limited to, autocamtide-2-related inhibitory peptide (AIP), CaM Kinase II inhibitor, diisopropylfluorophosphate, galanthamine hydrobromide, (±)-Hhuperzine A, quinacrine dihydrochloride, and pepstatin A Methyl Ester.

For instance, calcium-calmodulin ($Ca^{2+}$/CaM) kinase promoters may be selected from, but not limited to, Zic2.

For instance, diacylglycerol kinase inhibitor may be selected from, but not limited to, diacyglycerol kinase I inhibitors and diacyglycerol kinase II inhibitors. Preferably, the diacylglyercol kinase inhibitors may be selected from, but not limited to, 6-[2-[4-[(4-fluorophenyl)phenylmethylene]-1-piperidinyl]ethyl]-7-methyl-5H-thiazolo[3,2-a]pyrimidin-5-one (ALX), R59022, amidepsines A, B, and C, and RHC-80267.

Another embodiment of the invention is to provide a diagnostic kit for diagnosing ADHD or BD, and an agent identifying kit used for identifying a modulator of diacylglycerol signaling for the treatment of ADHD or BD. For instance, the modulator may include a calcium-calmodulin ($Ca^{2+}$/CaM) kinase inhibitor, a diacylglycerol kinase inhibitor, and a protein kinase C inhibitor. Preferably, the kit used for identifying a modulator that alters calcium-activated potassium channel activity such as $hSK_4$ channel activity. The kits include the buffers described herein, and preparation thereof.

The buffers that may be used in the diagnostic and agent identifying methods of the present invention include, but are not limited to, the buffers described in U.S. Pat. Nos. 7,425,410 and 7,906,300 which are hereby incorporated by reference in their entirety. These buffers include regular $K^+$-containing buffer which is a HEPES buffer to which potassium has also been added (5 mM KCl, 4 mM $NaHCO_3$, 5 mM HEPES, 134 mM NaCl, 2.3 mM $CaCl_2$, and 5 mM glucose) and is also referred to as "regular" or "stock" buffer at a pH of 7.4 (range of 7.3 to 7.5).

The present invention also provides an improved assay, device and methods of using the same to diagnose BD and ADHD.

The assay uses a reference buffer or regular buffer and a test buffer. The "reference buffer" or "regular buffer" contains only $Na^+$, $Ca^{2+}$, and HEPES without any other reagents. The "test buffer" containing no potassium ($K^+$-free buffer) is a HEPES buffer without potassium (4 mM $NaHCO_3$, 5 mM HEPES, 134 mM NaCl, 2.3 mM $CaCl_2$, and 5 mM glucose) and with a $K^+$ channel altering agent, at a pH of 6.8 (range of 6.6 to 7.0). The test buffer may also contain 30 μM ethacrynic acid dissolved in EtOH as solvent.

$K^+$ channel altering agents include, but are not limited to, ethanol, amphetamine, ephedrine, cocaine, caffeine, nicotine, methylphenidate, lithium, δ-9-tetrahydrocannibinol, phencyclidine, lysergic acid diethylamide (LSD), mescaline, or combinations thereof. Preferably, the $K^+$ channel altering agent is ethanol.

When the cells are suspended in a $K^+$ free buffer the intracellular $K^+$ leaks out. However the $Na^+K^+$-ATPase pump cannot compensate for this loss by bringing in the $K^+$ from outside the cell since there is no $K^+$ outside. This causes the $K^+$ channel to shut down. When a $K^+$ channel altering agent (such as ethanol) is added, the agent affects the $K^+$ channel, for instance, by opening the $K^+$ channel, thus further reducing the membrane potential. This opening depends on the patients from whom the cells were drawn. This difference is reflected in the MPR™ obtained as well as in the pathway governing the cell membrane potentials and excitabilities of the excitable cells.

The following examples are provided for illustrative purposes only and are in no way intended to limit the scope of the invention.

EXAMPLE 1

Discovering Diagnostic Markers for BD and ADHD

This invention discloses that the DAG signaling pathway modulates the MPR™ in BD and ADHD. Those skilled in the art recognize that this invention can be usefully employed in discovering new diagnostic markers by measuring the differential expression of these markers in the cells collected from BD and ADHD patients. It is demonstrated by this invention that the MPR™ can be modulated by the promoters and inhibitors of DAG, PKC and $Ca^{2+}$/CaM. It is contemplated that this could be used for the discovering additional diagnostic markers for these illnesses using patients' cells leading to personalized treatment.

EXAMPLE 2

Developing Drugs for BD and ADHD

Currently lithium is an effective drug for BD where as methylphenidate (trade name Ritalin) is an effective drug for ADHD. Lithium's toxicity and undesirable side effects are the important limitations limiting its widespread use. Similarly Ritalin is a highly addictive stimulant leading to its abuse by the patients. These limitations incentivize the need for the development of new and effective drugs for these diseases. Those skilled in the art recognize that the promoters and inhibitors of DAG, PKC and $Ca^{2+}$/CaM would be potential candidates. It is contemplated that they could be used for discovering additional drugs for these illnesses by using patient's cells. For example, the blood-brain barrier (BBB) excludes many highly hydrophilic compounds. To ensure that the effective compounds of the invention cross the BBB, if desired, they can be formulated, for example, in liposomes, or chemically derivatized. Engleton et al (Engleton et al., Peptides 9:1431-1439, 1997) have reviewed the strategies for increasing bioavailability of polypeptide drugs in the brain, and of methods for determining the permeability of polypeptides through the BBB using in vitro and in vivo assays. Strategies that have been successfully used to increase the permeability of other neuropeptides through the BBB are particularly contemplated. Furthermore RBCs are good pharmacological models for BD and ADHD. The influence of DAG pathway and its associated molecules affecting the MPR™ can be modulated by new drugs for BD and ADHD (Hinderling (1997) PHARMACOLOGICAL REVIEWS Vol. 49, No. 3).

EXAMPLE 3

In order to verify the CAK channel is involved in the membrane potential of the RBC used for the membrane potential ratios (MPR™) tests, the CAK channel blockers, quinine and clotrimazole were added to the test buffer and the membrane potential ratios (MPR™) was determined. The results are shown in FIG. 2. The membrane potential ratios (MPR™) values are shown in box plots. Box 2 shows the increased values of membrane potential ratios (MPR™) with 1 mM quinine in the test buffer as compared to the values in box 1 for the test buffer without quinine. Similarly boxes 3, 4 and 5 show the results for clotrimazole (CLTX). Box 3 represents no CLTX, while box 4 for 2.5 micro molar CLTX and box 5 for 5 micro molar concentrations in the test buffer. These blockers depolarized the membrane potentials strongly indicating the involvement of CaK in the MPR™ tests. This result establishes that the calcium activated potassium channels $hSK_4$ (KCNN4) expressed in RBC are responsible for the MPs observed in RBC.

EXAMPLE 4

The two most important pathways involved in the regulation of biological processes in the cell are the cAMP pathway and the DAG pathway. The cAMP pathway was considered first. 8-CPT-cAMP is a cAMP analog that promotes cAMP production in cells. In order to determine whether the cAMP pathway is involved in the membrane potential ratio (MPR™) test, 8-CPT-cAMP was added to the test buffer and the membrane potential ratios (MPR™) values were determined. As shown in FIG. 3, 8-CPT (50 micro molar) did not have any effect on the membrane potentials. Based on these results it was concluded that the cAMP pathway did not play a role modulating the membrane potential ratio (MPR™).

EXAMPLE 5

The DAG signaling pathway was considered. One of the important proteins in this pathway is protein kinase C (PKC). Phorbol 12-Myristate 13-Acetate (PMA) is an effective promoter of PKC. FIG. 4 shows the results of a comparison of the membrane potential ratio (MPR™) values with 2.5 μM PMA in the test buffer and those values without PMA. PMA was shown to depolarize the cells very effectively. This result establishes that the DAG signaling pathway is involved in modulating the membrane potential ratio (MPR™).

EXAMPLE 6

In order to further confirm the involvement of the DAG pathway in modulating the membrane potential ratio (MPR™), the PKC inhibitor, staurosporine, was added to the test buffer at three different concentrations (250 nM, 500 nM and 750 nM) and the membrane potential ratio (MPR™) values determined and shown in FIG. 5. Staurosporine was shown to hyperpolarizes the membrane potentials very effectively indicating the role of PKC and the DAG pathway in modulating the membrane potential ratio (MPR™).

EXAMPLE 7

Figure 6:
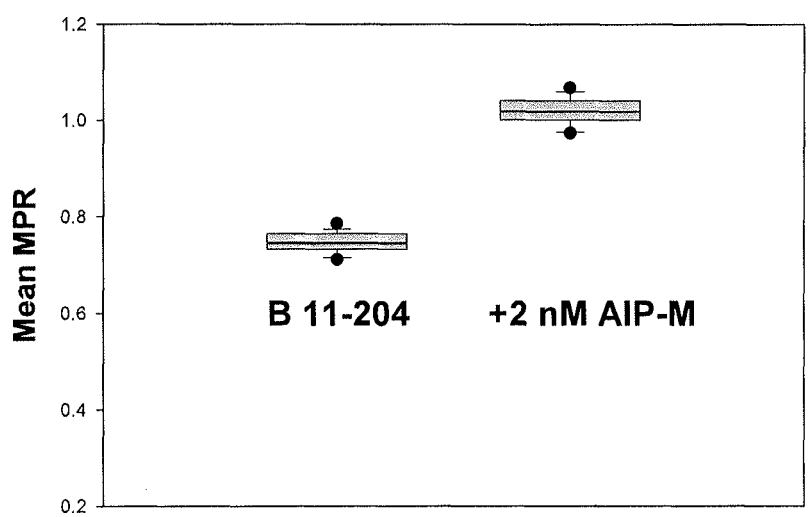
FIG. 6. Shows the effect of AIP-M on membrane potential ratio (MPR™).

Another important enzyme in the DAG signaling pathway is CaM Kinase II which participates in the $Ca^{2+}$/CaM modulation of the calcium-activated potassium (CAK) channels. AIP (Autocamtide-2-related Inhibitory Peptide), a novel synthetic peptide, is a CaM Kinase II Inhibitor. A nonphosphorylatable analog of AIP, AIP (myristoylated), was found to be a highly specific and potent inhibitor of calmodulin-dependent protein kinase II (CaM-kinase II). AIP (myristoylated) is the same as AIP but is myristoylated at the N-terminus to increase cell permeability. As shown in FIG. 6, AIP depolarizes the membrane potential robustly at a 5 µM concentration, establishing the critical role of the DAG signaling pathway in modulating membrane potential ratio (MPR™).

EXAMPLE 8

Figure 7:
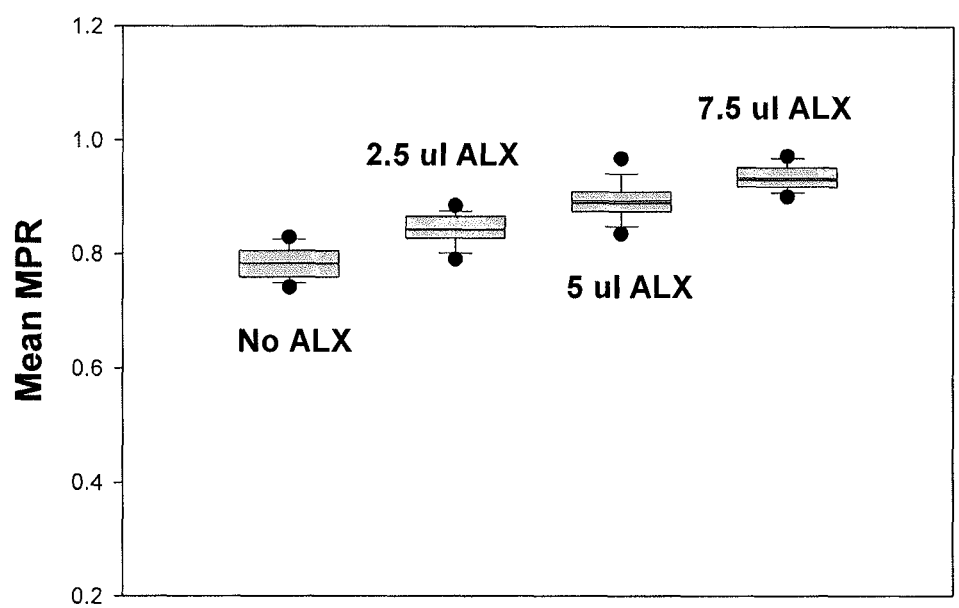
FIG. 7. Shows the effect of DGK Inhibitor ALX on membrane potential ratio (MPR™).

FIG. 7 shows the effect of DAG Kinase inhibitor, ALX, (6-[2-[4-[(4-fluorophenyl)phenylmethylene)-1-piperidinyl]ethyl]-7-methyl-5H-thiazolo[3,2-a]pyrimidin-5-one on the membrane potential ratio (MPR™). ALX depolarized the membrane potential at three different concentrations including 2.5 µl, 5 µl and 7.5 µl establishing the critical role of DAG signaling pathway in modulating the membrane potential ratio (MPR™).

EXAMPLE 9

Blood samples from a patient were suspended in a reference buffer (reference buffer sample) as well as in a test buffer (test buffer sample) with 3,3'-dihexyloxacarbocyanine iodide ($DiOC_6$) dye, incubated, spun, drained and the supernatants resuspended in their respective buffers without the dye. The resuspended buffer samples were then distributed in three separate 96 well plates and tested in a Plate Reader for fluorescence intensity. The Plate Reader recorded a data matrix of each of the 96 well plates and the data matrix was transferred to a Template to calculate the ratio between the test buffer sample and the corresponding reference buffer sample. The resulting ratios were calculated to determine the mean value, the standard deviation and the coefficient of variation. This procedure was repeated two more times and the resulting mean value, standard deviation and the coefficient of variation calculated in the same manner. The Membrane Potential Ratio (MPR™) obtained from the mean values was 0.781 (with a standard deviation of 0.014 and coefficient of variation of 1.76). Based on the MPR™ value of 0.781, the patient was diagnosed to have ADHD (with a greater than 97% probability).

The invention claimed is:

1. A method of identifying an agent for treatment of bipolar disorder (BD) comprising:
    combining a first population of human BD patient cells comprising cells that express human calcium-activated potassium-channels $hSK_4$, with a test agent suspected of altering human calcium-activated potassium channels $hSK_4$ activity;
    obtaining a test ratio of a mean membrane potential of the first population of human BD patient cells incubated in vitro in the presence of the test agent and in the absence of $K^+$, to a mean membrane potential of a second population of the human patient cells incubated in vitro in the absence of the test agent and the presence of $K^+$ or absence of $K^+$;
    comparing the test ratio to (a) and/or (b):
    (a) a control ratio of a mean membrane potential from control human cells known to not have BD comprising cells that express human calcium-activated potassium-channels $hSK_4$, incubated in vitro in the presence of an agent that alters human calcium-activated potassium channels $hSK_4$ activity and in the absence of $K^+$, to a mean membrane potential of the control human cells incubated in vitro in the absence of the agent that alters human calcium-activated potassium channels $hSK_4$ activity and in the presence of $K^+$ or absence of $K^+$,
    (b) a bipolar control ratio of a mean membrane potential from bipolar control human cells known to have BD comprising cells that express human calcium-activated potassium-channels $hSK_4$, incubated in vitro in the presence of the agent that alters human calcium-activated potassium channels $hSK_4$ activity and in the absence of $K^+$, to a mean membrane potential of the bipolar control human cells incubated in vitro in the absence of the agent that alters human calcium-activated potassium channels $hSK_4$ activity and in the presence of $K^+$ or absence of $K^+$;
    wherein when:
    (1) the test ratio is not significantly different from the control ratio of (a),
    (2) the test ratio is increased towards the control ratio in comparison to the bipolar control ratio of (b), or
    (3) the test ratio is increased in comparison to the bipolar ratio of (b), the test agent modulates the mean membrane potential in BD patients.

2. The method of claim 1, wherein the agent is selected from the group consisting of a calcium-calmodulin ($Ca^{2+}$/CaM) kinase inhibitor, a diacylglycerol kinase inhibitor, and a PKC inhibitor.

3. The method of claim 2, wherein the agent is a calcium-calmodulin ($Ca^{2+}$/CaM) kinase inhibitor.

4. The method of claim 3, wherein the calcium-calmodulin ($Ca^{2+}$/CaM) kinase inhibitor is autocamtide-2-related inhibitory peptide (AIP).

5. The method of claim 2, wherein the agent is a diacylglycerol kinase inhibitor selected from the group consisting of 6-[2-[4-[(4-fluorophenyl)phenylmethylene]-1-piperidinyl]ethyl]-7-methyl-5H-thiazolo[3,2-a]pyrimidin-5-one (ALX).

6. The method of claim 5, wherein the diacylglycerol kinase inhibitor is 6-[2-[4-[(4-fluorophenyl)phenylmethylene]-1-piperidinyl]ethyl]-7-methyl-5H-thiazolo[3,2-a]pyrimidin-5-one (ALX).

7. A method of identifying an agent that modulates diacylglycerol signaling for the treatment of bipolar disorder (BD) comprising:

combining a first population of human BD patient cells and a test agent suspected of altering diacylglycerol signaling;

obtaining a test ratio of a mean membrane potential of the first population of human BD patient cells incubated in vitro in the presence of the test agent and in the absence of $K^+$, to a mean membrane potential of a second population of the human BD patient cells incubated in vitro in the absence of the test agent and presence of $K^+$;

comparing the test ratio to (a) and or (b):

(a) a control ratio of a mean membrane potential from control human cells known to not have BD incubated in vitro in the presence of an agent that alters diacylglycerol signaling and in the absence of $K^+$, to a mean membrane potential of the control human cells known incubated in vitro in the absence of the agent that alters diacylglycerol signaling and in the presence of $K^+$, (b) a bipolar control ratio of a mean membrane potential from bipolar control human cells known to have said BD incubated in vitro in the presence of the agent that alters diacylglycerol signaling and in the absence of $K^+$, to a mean membrane potential of the bipolar control human cells incubated in vitro in the absence of the agent that alters diacylglycerol signaling and in the presence of $K^+$ or absence of $K^+$;

wherein when:

(1) the test ratio is not significantly different from the control ratio of (a), (2) the test ratio is increased towards the control ratio in comparison to the bipolar control ratio of (b), or (3) the test ratio is increased in comparison to the bipolar ratio of (b), the test agent modulates the mean membrane potential in BD patients.

8. The method of claim 7, wherein the human cells is selected from the group consisting of red blood cells and lymphoblasts.

9. The method of claim 7, wherein the agent is selected from the group consisting of a calcium-calmodulin ($Ca^{2+}$/CaM) kinase inhibitor and a diacylglycerol kinase inhibitor.

10. The method of claim 7, wherein the agent is a calcium-calmodulin ($Ca^{2+}$/CaM) kinase inhibitor.

11. The method of claim 10, wherein the calcium-calmodulin ($Ca^{2+}$/CaM) kinase inhibitor is autocamtide-2-related inhibitory peptide (AIP).

12. The method of claim 7, wherein the agent is a diacylglycerol kinase inhibitor.

13. The method of claim 12, wherein the diacylglycerol kinase inhibitor is 6-[2-[4-[(4-fluorophenyl)phenylmethylene]-1-piperidinyl]ethyl]-7-methyl-5H-thiazolo[3,2-a]pyrimidin-5-one (ALX).

14. A method of identifying an agent for treatment of bipolar disorder (BD) of claim 7, wherein:

the first population of human BD patient cells is combined with a test agent suspected of altering $Ca^{2+}$/CaM activation of calcium-activated potassium channels, the control human cells and the bipolar control human cells are incubated in vitro in the presence of autocamtide-2-related inhibitory peptide (AIP), the human cells are selected from the group consisting of red blood cells and lymphoblasts, and the $Ca^{2+}$/CaM activation of calcium-activated potassium channels depolarizes the mean membrane potential of the human BD patient cells.

15. A method of identifying an agent for treatment of bipolar disorder (BD) of claim 7, wherein:

the first population of human BD patient cells is combined with a test agent suspected of altering diacylglycerol kinase activity, the control human cells and the bipolar control human cells are incubated in vitro in the presence of 6-[2-[4-[(4-fluorophenyl)phenylmethylene]-1-piperidinyl]ethyl]-7-methyl-5H-thiazolo[3,2-a]pyrimidin-5-one (ALX), and the human cells are selected from the group consisting of red blood cells and lymphoblasts.

* * * * *